United States Patent [19]
Royster, Jr. et al.

[11] Patent Number: 5,871,896
[45] Date of Patent: Feb. 16, 1999

[54] PREPARATION AND USE OF A DIMETHYLAMINE SILVER BROMIDE COMPLEX AS A SINGLE SOURCE PRECURSOR FOR NUCLEATION OF SILVER BROMIDE CRYSTALS

[75] Inventors: Tommie L. Royster, Jr., Rochester; David E. Fenton, Fairport; Seshadri Jagannathan; Joseph J. Tiberio, both of Rochester, all of N.Y.

[73] Assignee: Eastman Kodak Company, Rochester, N.Y.

[21] Appl. No.: 866,855

[22] Filed: May 30, 1997

[51] Int. Cl.$^6$ ............................ G03C 1/005; C01G 5/00; C01G 5/02; C07F 1/10
[52] U.S. Cl. ............................ 430/569; 423/23; 423/42; 117/938; 205/507; 556/110
[58] Field of Search ................................ 430/569; 423/23, 423/42; 117/938; 205/507; 556/110

[56] References Cited

U.S. PATENT DOCUMENTS

| | | | |
|---|---|---|---|
| 3,883,355 | 5/1975 | Walworth | 430/569 |
| 3,941,600 | 3/1976 | Walworth | 430/569 |
| 4,153,462 | 5/1979 | Gerber et al. | 430/569 |
| 4,340,666 | 7/1982 | Walworth | 430/569 |
| 5,478,718 | 12/1995 | Verbeeck et al. | 430/569 |
| 5,541,051 | 7/1996 | Verbeeck et al. | 430/569 |
| 5,604,087 | 2/1997 | Lapp et al. | 430/569 |
| 5,759,762 | 6/1998 | Budz et al. | 430/611 |

OTHER PUBLICATIONS

Beilstein Database, Beilstein Reg. No. 4921664, Mar. 1998.

*Primary Examiner*—Mark F. Huff
*Attorney, Agent, or Firm*—Arthur H. Rosenstein

[57] ABSTRACT

A dimethylamine silver bromide complex is used as a single source precursor for nucleation of silver bromide crystals.

8 Claims, No Drawings

PREPARATION AND USE OF A DIMETHYLAMINE SILVER BROMIDE COMPLEX AS A SINGLE SOURCE PRECURSOR FOR NUCLEATION OF SILVER BROMIDE CRYSTALS

FIELD OF THE INVENTION

This invention relates to the nucleation process of silver bromide crystals. In particular, it relates to the use of a unique silver halide complex contained in a dimethylamine hydrobromide solution that can be used as single source material for nucleation of silver bromide crystals.

BACKGROUND OF THE INVENTION

Silver halide emulsions are generally prepared using a reactive precipitation process; aqueous solutions of silver nitrate and alkali halides are reacted in the presence of gelatin. The composition of resultant product (silver halide emulsions) is tuned by varying the constituents of the alkali halide solution. For example, the precipitation of silver bromide emulsions is carried out using sodium bromide as the alkali halide, while silver bromoiodide emulsions are precipitated using a mixture of sodium bromide and potassium iodide. Appropriate addenda/dopants are generally introduced as aqueous solutions during the precipitation process, to generate silver halide emulsions of desired composition.

The important feature of all these processes is the bimolecular chemical reaction between (Ag+) ions and the appropriate anion(s) to generate the precipitating species. It is possible to vary the chemical and the structural composition of the product emulsion by varying the constituents of the reagent solutions, but the chemical reaction responsible for the generation of the desired silver halide emulsion is always the reaction between (Ag+) ions that are present in a solution or on the surface of the silver halide emulsion, and the appropriate anion(s).

From an operational point of view, generation of silver halide emulsions by this reactive precipitation process involves the addition of concentrated reagent solutions into a reactor under vigorous mixing conditions. The goal of the mixing process is to minimize the volume of the reactor that is exposed to the unreacted reagent solutions. However, even under ideal mixing conditions, the volume of the reactor that is exposed to the unreacted reagents is finite and relatively large.

In order to understand the reasons for the exposure of the reactor contents to unreacted reagents it is necessary to examine the mechanism of the mixing process. Mixing in emulsion precipitation processes is achieved by means of a rapidly spinning rotary agitator. The momentum generated by the rotary agitator results in the circulation of the fluid in the reactor. Appropriate baffling devices are used to randomize the fluid motion in the reactor, to achieve efficient mixing. It is important to recognize that efficient mixing requires rapid circulation of the fluid in the reactor. In a typical emulsion generation process, the reagent solutions are introduced into a region of the reactor that experiences good mixing. Consequently, the concentrated reagent solutions are introduced into a region of the reactor that experiences rapid circulation of the fluid in the reactor; i.e. the reagent introduction region in the reactor is exposed frequently to the contents of the reactor.

It is also important to recognize that efficient mixing is necessary at the reagent introduction region, in order to promote the reaction between the concentrated reagents. Because this (efficient) mixing process is carried out by rapid circulation of the reactor fluid through the reagent introduction region, the contents of the reactor are necessarily exposed to the concentrated reagents. From a kinetic view point, the extent of exposure of the reactor contents to the unreacted reagents would depend on the rate of dilution of the concentrated reagents relative the rate of the chemical reaction between the concentrated reagents. Under ideal mixing conditions, the rate of dilution of the concentrated reagents is determined by the molecular/ionic diffusivity of the reactant species; which is still considerably smaller than the rate of the relevant chemical reactions. Hence, the extent of exposure of the reactor contents to the unreacted reagents can be significant even under ideal mixing conditions.

The unintentional exposure of the reactor contents to the unreacted reagents can have undesired effects on the emulsion crystals. For example, exposure of unreacted silver nitrate can result in the creation of fog centers in the crystals.

Furthermore, consistent nucleation conditions are critical to repeatable precipitations. Double jet nucleation using solutions of silver nitrate and soluble halides, depend critically on matched kettle reagent arrival times in the reactor. Small variations in the mixing of the reactants upon arrival in the reactor can result in high levels of variability in emulsion grain size or size distribution. Hence, nucleation is generally carried out under conditions of relatively high halide concentrations (high pAg) in order to ameliorate pAg shifts associated with any mismatch in the solution properties or arrival times.

The use of concentrated solutions of silver halide complexes prepared from methylamineformamide and excess halide have been reported as a method for alleviating these concerns. However, methylamineformamide is exceedingly hazardous, and the solvent has been documented as a teratogen (promotes deformity in embryos).

SUMMARY OF THE INVENTION

This invention addresses the need for reducing process variability inherent in double jet precipitation of silver bromide crystals. A solution of hydrated dimethylamine hydrobromide ($[Me_2NH_2]Br$) containing the silver bromide precursor complex $[Me_2NH_2]_x[Ag_mBr_n]$, is disclosed as a single source material for silver bromide nucleation processes (as opposed to the prior art of nucleation by double jet precipitation). The solution containing $[Me_2NH_2]_x$ $[Ag_mBr_n]$ removes the need to manage two separate reagents for the critical nucleation step in silver bromide precipitation.

DETAILED DESCRIPTION OF THE PREFERRED EMBODIMENTS

Hydrated $[Me_2NH_2]Br$ solutions containing novel silver bromide complexes are used as single source materials for nucleation of silver bromide crystals. Solutions containing the silver bromide precursor complex $[Me_2NH_2]_x[Ag_mBr_n]$ (where n=m+x and wherein n is 2, x is 1 and m is 1, wherein n is 3, x is 2 and m is 1, wherein n is 4, x is 2 and m is 2, wherein n is 5, x is 3, and m is 2) can be prepared from the following reactions.

i) $AgBr \xrightarrow{[Me_2NH_2]Br} [Me_2NH_2]_x [Ag_mBr_n]$

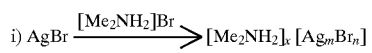

ii) $AgNO_3 \xrightarrow{[Me_2NH_2]Br} [Me_2NH_2]_x [Ag_mBr_n]$

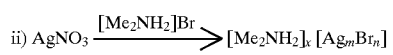

-continued iii) [Me₂NH₂]₃ [Ag₂Br₅] 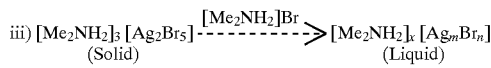 [Me₂NH₂]ₖ [AgₘBrₙ]
(Solid)  (Liquid)

This invention uses the solutions prepared from the above reactions as single source materials for the nucleation of silver bromide crystals. The nucleation process is accomplished by introducing excess water to the hydrated [Me₂NH₂]Br solutions containing the precursor complex [Me₂NH₂]ₖ[AgₘBrₙ].

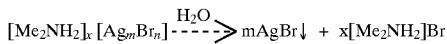 
[Me₂NH₂]ₖ [AgₘBrₙ] →$^{H_2O}$ mAgBr↓ + x[Me₂NH₂]Br

Thus, the amine salt [Me₂NH₂]Br can be hydrated and combined with either AgBr or AgNO₃ to form solutions containing [Me₂NH₂]ₓ[AgₘBrₙ]. Alternatively, the complex [Me₂NH₂]₃[Ag₂Br₅] can be isolated and dissolved in hydrated [Me₂NH₂]Br. These solutions are then used as single source materials for nucleation of silver bromide crystals.

The following examples illustrate the invention.

EXAMPLE 1

Method A

In a sealed vessel, hydrated [Me₂NH₂]Br was heated to approximately 70° C. Then, hydrated silver nitrate was introduced while stirring. The mixture was stirred under the sealed conditions until the silver bromide that initially formed was complexed and a clear colorless solution was observed. The solution was then removed from the heat and allowed to cool to room temperature. Depending on the concentration needed, the final solution contained an amine/silver mol ratio of ≧13. The water/amine mol ratio ranged from 1–2.

Method B

Hydrated [Me₂NH₂]Br was combined with silver bromide in a sealed vessel and the mixture heated to approximately 70° C. The mixture was stirred until a clear colorless solution was observed. Depending on the concentration needed, the final solution contained an amine/silver mol ratio of ≧13. The water/amine mol ratio ranged from 1–2.

Method C

The amine salt [Me₂NH₂]Br was combined with silver bromide using a mol ratio of 3:2 in dimethyl formamide (DMF) solvent (the equivalent amount of concentrated HBr can be substituted for [Me₂NH₂]Br). The mixture was then heated on a steambath until a clear colorless solution was observed. After cooling to room temperature, the solution was layered with diethyl ether and allowed to stand for 16 h. Crystals of the complex [Me₂NH₂]₃[Ag₂Br₅] were isolated after decanting or filtering the solution followed by washing the material with diethyl ether. The isolated complex was then dissolved in the hydrated [Me₂NH₂]Br.

The advantages of this chemistry are illustrated with the following examples:

EXAMPLE 2

A kettle containing 3950 g of water, 28 g of sodium bromide and 16 g of gel was heated to 45° C. During a five second period, 16.1 ml of an aqueous solution containing 0.746 g of silver nitrate and 16.1 ml of an aqueous solution containing 0.452 g of sodium bromide were added at constant flow rate. During the following six minutes, the temperature of the kettle was raised linearly to 55° C. Ten minutes after reaching temperature, 4000 ml of an aqueous solution containing 80 g gel was added. Subsequent steps in the precipitation were held at a constant pAg of 9.54 by addition of aqueous sodium bromide solution; solution A. The aqueous silver nitrate solution used is listed as solution B. Solution A: water 4444 grams, NaBr 469.72 grams. Solution B: water 3489.1 grams, AgNO₃ 612.3 grams.

Over the next 6 minutes and 9 seconds, 215 ml of solution B was added at a constant rate. Immediately following and for the next 17 minutes and 42 seconds, 929.3 ml of solution B was added at a linearly increasing rate starting at 35 ml/min. Finally 1858.5 ml of solution B was added. The kettle was cooled and sizing samples shown on Table 1 were taken.

EXAMPLE 3

Solution C was stirred and heated at 80° C. for 1 hour and then cooled to 60° C. prior to use in nucleation. Solution C: 18.998 g [Me₂NH₂]Br, 2.70 g of water, and 0.824 g AgBr.

A kettle containing 3954 g of water, 14.4 g of sodium bromide and 16 g of gel was heated to 45° C. For 30 seconds preceding addition of solution C, 80° C. water was added to the kettle, then solution C was added over a period of 5 seconds at constant flow, then for 30 more seconds 80° C. water was added. During the following 6 minutes, the temperature of the kettle was raised linearly to 55° C. Subsequently, the precipitation was performed in a manner identical to Example 2.

EXAMPLE 4

A kettle containing 3957 g of water 0.145 g of sodium bromide and 16 g of gel was heated to 45° C. For 30 seconds preceding addition of solution C, 80° C. water was added to the kettle, then solution was added over a period of 5 seconds at constant flow, then for 30 more seconds 80° C. water was added. Then 104 g of an aqueous solution containing 9.95 g of NaBr was added. During the following 6 minutes, the temperature of the kettle was raised linearly to 55° C. Subsequently, the precipitation was performed in a manner identical to the prior art method.

TABLE 1

| Equivalent Circular Diameter (ECDs) | |
|---|---|
|  | ECD (microns) |
| Example 2 | 2.66 |
| Example 3 | 2.50 |
| Example 4 | 2.69 |

All three examples were very thin, and in electron micrographs, visually indistinguishable from each other.

The two examples show that nearly identical emulsions can be made using a single source to replace the standard double-jet nucleation. Furthermore, the results appear to be relatively independent of nucleation pAg. Finally, the precipitations using the single source [Me₂NH₂]ₖ[AgₘBrₙ] material are substantially more robust and repeatable.

While the invention has been described with particular reference to a preferred embodiment, it will be understood by those skilled in the art the various changes can be made and equivalents may be substituted for elements of the preferred embodiment without departing from the scope of the invention. In addition, many modifications may be made to adapt a particular situation in material to a teaching of the invention without departing from the essential teachings of the present invention.

We claim:

1. A method of preparing a solution of a dimethylamine silver bromide complex comprising reacting $[(CH_3)_2NH_2]Br$ with AgBr and water.

2. A method of preparing a solution of a dimethylamine silver bromide complex comprising reacting $[(CH_3)_2NH_2]Br$ with silver nitrate and water.

3. A solution of a silver bromide complex comprising $[(CH_3)_2NH_2]_x[Ag_mBr_n]$ and water and dimethylamine hydrobromide wherein if n=2, x is 1 and m is 1, if n=3, x is 2 and m is 1, if n is 4, x is 2 and m is 2 and if n is 5, x is 3 and m is 2.

4. A method of preparing a solution of a dimethylamine silver bromide complex comprising $[(CH_3)_2NH_2]_3[AgBr_5]$, $[(CH_3)_2NH_2]Br$, and water.

5. The method of precipitating silver bromide by introducing the solution containing $[(CH_3)_2NH_2]_x[Ag_mBr_n]$, dimethylamine hydrobromide and water into an aqueous medium wherein, if n=2, x=1, m=1; if n=3, x=2, m=1; if n=4, x=2, m=2; and if n=5, x=3, m=2.

6. Isolating $[(CH_3)_2NH_2]_3[Ag_2Br_5]$ as a crystalline material by combining $[(CH_3)_2NH_2]Br$ with AgBr in dimethylformamide in a 3:2 molar ratio or isolating $[Me_2NH_2]_3[Ag_2Br_5]$ by combining concentrated HBr with AgBr in dimethylformamide in a 3:2 molar ratio wherein the isolation is accomplished by washing after filtration.

7. A crystalline material having the structure: $[(CH_3)_2NH_2]_3[Ag_2Br_5]$.

8. A method of nucleating silver bromide crystals comprising precipitating them from solutions of $[(CH_3)_2NH_2]_x[Ag_mBr_n]$, dimethylamine hydrobromide and water wherein if n=2, x is 1 and m is 1, if n=3, x is 2 and m is 1, if n is 4, x is 2 and m is 2 and if n is 5, x is 3 and m is 2.

* * * * *